United States Patent
Hartley et al.

(10) Patent No.: US 7,846,194 B2
(45) Date of Patent: Dec. 7, 2010

(54) ILIAC ARTERY STENT GRAFT

(75) Inventors: David Ernest Hartley, Subiaco (AU); Krasnodar Ivancev, Lund (SE)

(73) Assignees: William A. Cook Australia Pty. Ltd., Brisbane (AU); William Cook Europe ApS, Bjaeverskov (DK); Cook Incorporated, Bloomington, IN (US)

( * ) Notice: Subject to any disclaimer, the term of this patent is extended or adjusted under 35 U.S.C. 154(b) by 17 days.

(21) Appl. No.: 11/444,688

(22) Filed: Jun. 1, 2006

(65) Prior Publication Data

US 2006/0287704 A1 Dec. 21, 2006

Related U.S. Application Data (60) Provisional application No. 60/686,252, filed on Jun. 1, 2005.

(51) Int. Cl.
*A61F 2/06* (2006.01)

(52) U.S. Cl. .............. 623/1.13; 623/1.15; 623/1.16

(58) Field of Classification Search ............... 623/1.35, 623/1.15, 1.23, 1.13, 1.44, 1.16; *A61F 2/06*
See application file for complete search history.

(56) References Cited

U.S. PATENT DOCUMENTS

| | | | | |
|---|---|---|---|---|
| 5,755,778 A | * | 5/1998 | Kleshinski | 623/1.13 |
| 6,811,566 B1 | * | 11/2004 | Penn et al. | 623/1.15 |
| 6,949,121 B1 | * | 9/2005 | Laguna | 623/1.35 |
| 7,018,400 B2 | * | 3/2006 | Lashinski et al. | 623/1.11 |
| 7,326,242 B2 | * | 2/2008 | Eidenschink | 623/1.15 |
| 2002/0193873 A1 | * | 12/2002 | Brucker et al. | 623/1.35 |
| 2003/0097169 A1 | * | 5/2003 | Brucker et al. | 623/1.11 |
| 2003/0158594 A1 | * | 8/2003 | Kang et al. | 623/1.13 |
| 2004/0054403 A1 | * | 3/2004 | Israel | 623/1.35 |
| 2004/0138732 A1 | * | 7/2004 | Suhr et al. | 623/1.11 |
| 2005/0119731 A1 | * | 6/2005 | Brucker et al. | 623/1.35 |
| 2005/0171598 A1 | * | 8/2005 | Schaeffer | 623/1.35 |
| 2006/0136031 A1 | * | 6/2006 | Gallo et al. | 623/1.11 |

* cited by examiner

*Primary Examiner*—William H Matthews
*Assistant Examiner*—Jason-Dennis Stewart
(74) *Attorney, Agent, or Firm*—Richard J. Godlewski (57) ABSTRACT

A side branch stent graft (1) suitable for the iliac arteries has a main tubular body (3) of a biocompatible graft material and a tubular side branch (5). The tubular side branch is affixed into the main tubular body so that a side branch lumen is in fluid communication with a main lumen. There is at least one external zig-zag stent (13) on the main tubular body proximal of the tubular side branch, one central external stent (14) which also encompasses the side arm, at least one external zig-zag stent (16) on the main tubular body distal of the tubular side branch and one internal zig-zag stent (15) at the distal end of the main tubular body. A reinforcing ring (9) is around the proximal end of the main tubular body and stitched thereto.

17 Claims, 7 Drawing Sheets

*Fig 11*

ILIAC ARTERY STENT GRAFT

CROSS-REFERENCE TO RELATED APPLICATIONS

This application claims priority of provisional application Ser. No. 60/686,252, filed Jun. 1, 2005.

TECHNICAL FIELD

This invention relates to a medical device and more particularly to the construction and deployment of a stent graft for the iliac artery

BACKGROUND OF THE INVENTION

The invention will be generally discussed with reference to a branched stent graft which can be deployed so that its branch is directed towards an internal iliac artery from the common iliac but is not so limited and may be used with deployment into any branched vessel but is particularly applicable where the vessel into which the device is deployed is a blind vessel, that is, access is not available from an end of the vessel remote from the bifurcation from a main vessel.

Stent grafts are used for treatment of vasculature in the human or animal body to bypass a repair or defect in the vasculature. For instance, a stent graft may be used to span an aneurism which has occurred in or associated with the iliac artery. In many cases, however, such a damaged or defective portion of the vasculature may include a branch vessel such as an internal iliac artery. Bypassing such a branch vessel without providing blood flow into it can cause problems and hence it has been proposed to provide a side branch on a stent graft which when deployed is positioned over the opening to the internal iliac artery and then another stent graft can be deployed through the side branch into the internal iliac artery to provide a blood flow path to the internal iliac artery.

Generally, when deploying an endovascular stent graft into a body lumen, it is possible to obtain access to such a body lumen from each end of the lumen where necessary, thereby facilitating placement of a device in the lumen. The internal iliac artery which extends from the common iliac artery below the aortic bifurcation is for all intents and purposes a blind vessel because there is no practical way of performing an endovascular minimally invasive procedure into that vessel other than by entry from the common iliac artery. The term blind vessel is used herein to describe such a vessel.

There have been proposals to deploy a branched stent graft into the common iliac artery via a femoral artery from a femoral incision with the branched stent graft having a side arm to extend into or at least adjacent the internal iliac artery, however, the use of such devices is very dependent upon favourable layout of the arteries and in many cases, access is extremely difficult. Access over the aortic bifurcation has been proposed but as there is limited distance between the aortic bifurcation and the iliac bifurcation special construction of a stent graft for this region is desirable.

It is the object of this invention therefore to provide a stent graft for deployment particularly into the iliac arteries or at least to provide a physician with a useful alternative.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefore the invention is said to reside in a side branch stent graft comprising a main tubular body of a biocompatible graft material and having a main lumen therethrough, a tubular side branch having a side branch lumen therethrough, the tubular side branch being affixed into the main tubular body so that the side branch lumen is in fluid communication with the main lumen, at least one external zig-zag stent on the main tubular body proximal of the tubular side branch, at least one external zig-zag stent on the main tubular body distal of the tubular side branch, one internal zig-zag stent at the distal end of the main tubular body, and a reinforcing ring around the proximal end of the main tubular body and stitched thereto.

Preferably there are one or two external zig-zag stents proximal of the tubular side branch and from one to three external zig-zag stents distal of the tubular side branch.

The reinforcing ring around the proximal end of the tubular body can comprise at least two turns of nitinol wire, each end of the nitinol wire terminating in a loop.

Preferably the tubular side branch comprises a connection socket for an extension stent. In one embodiment the connection socket comprises a first resilient ring around the tubular side branch at a distal end thereof, a second resilient ring spaced apart along the tubular side branch from the first ring and a zig zag resilient stent between the first and second rings. The zig zag resilient stent and the first and second rings are preferably on the outside of the tubular body and the first and second rings preferably comprise shape memory wire. The first and second rings preferably comprise at least two turns of wire with each end terminating in a loop.

The zig zag resilient stent of the connection socket preferably comprises a shape memory wire and the zig zag resilient stent defines a cylindrical form having a diameter less than that of the tubular side branch whereby to define a self contracting stent.

In a further form the invention comprises a side arm stent graft comprising a main tubular body of a biocompatible material, a fenestration in the main tubular body defined by a peripheral edge and a side arm being a tube of biocompatible material being joined around the peripheral edge at a joined region by stitching and extending from the main tube at an acute angle thereto and being in fluid communication with the main tubular body, at least one external zig-zag stent on the main tubular body proximal of the side arm, at least one external zig-zag stent on the main tubular body distal of the side arm, one internal zig-zag stent at the distal end of the main tubular body, and a reinforcing ring around the proximal end of the main tubular body and stitched thereto.

Preferably the fenestration is selected from the group comprising an elongate aperture, a substantially rectangular aperture, a substantially elliptical aperture and a substantially triangular aperture. The acute angle may be in the range of from 15 to 60 degrees and preferably 15 to 45 degrees.

The or each external zig-zag stents proximal of the tubular side branch can have a length of 14 mm and are spaced apart by about 2 mm and the or each external zig-zag stents distal of the tubular side branch has a length of 12 mm and are spaced apart by about 5 mm.

There may be further a central external zig-zag stent around the main tubular body and the tubular side branch. The central external zig-zag stent can have a length of 14 mm and is spaced apart from the stent proximal to it by about 2 mm and from the stent distal of it by about 5 mm.

The main tubular body can have a diameter of from 12 mm in a central portion and remaining at 12 mm or expanding to 20 mm at a proximal end with a frustoconical portion between the 12 mm and 20 mm portions and the tubular side branch has a diameter of about 8 mm. Alternatively the main tubular body can have a diameter of about 12 mm proximal of the tubular side branch and in a central portion and a diameter distal of the tubular side branch of from about 10 mm to 16 mm frustoconical portion between the 12 mm and 16 mm portions.

The main tubular body can have a length of about 69 mm to 119 mm and the tubular side branch has a length of about 25 mm. The stent graft can have a length from its proximal end to the distal end of the side arm of about 45 mm to 61 mm. The stent graft can have a length from its distal end to the distal end of the side arm of about 24 mm to 58 mm.

BRIEF DESCRIPTION OF THE DRAWING

This then generally describes the invention but to assist with the understanding, reference will now be made to the accompanying drawings which show preferred embodiments of the invention.

In the drawings.

DETAILED DESCRIPTION

Figure 1:
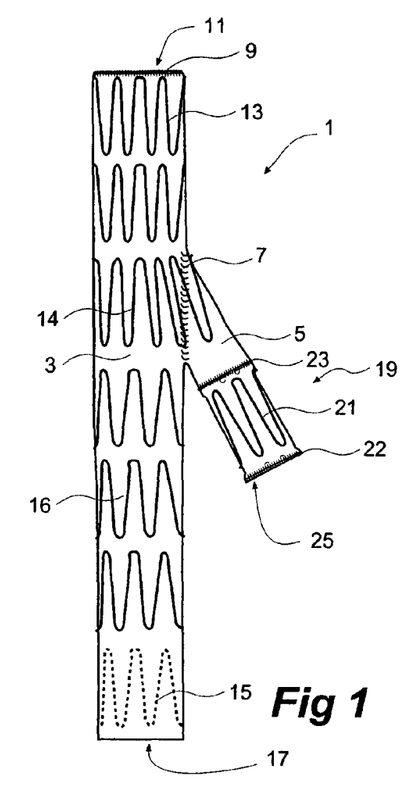
FIG. 1 shows a first embodiment of a stent graft of the present invention intended for use in the iliac artery.

Now looking more closely at the drawings and in particular FIG. 1 it will be seen that a stent graft 1 comprises a tubular body 3 with a side arm 5, also a tubular body, stitched into an aperture in the main body 3 at 7 so as to allow fluid communication from the lumen of the main body into the lumen of the side arm 5. The main tubular body 3 has a reinforcing ring arrangement 9 at its proximal end 11. The construction of the reinforcing ring 9 will be discussed in relation to FIG. 10. The tubular body 3 also has a number of external zig-zag self-expanding stents 13, 14 and 16 along its length and an internal self-expanding zig-zag stent 15 at its distal end 17.

PCT Patent Publication WO 2006/034276 entitled "Side Branch Stent Graft" includes discussion of one method of connection of a side arm to a main tubular body in a stent graft and the disclosure of this patent specification is incorporated herewith in its entirety.

On the side arm 5 there is a connection socket arrangement 19. The connection socket arrangement includes a self-expanding stent 21 between two reinforcing rings 22 and 23.

PCT Patent Publication WO 2006/034340 entitled "Stent Graft Connection Arrangement" discloses a stent graft connection arrangement of the type suitable for the side arm of the stent graft of the present invention, and the disclosure of that patent application is included herewith by reference in its entirety.

In the side arm stent graft shown in FIG. 1 there are two external stents 13 proximal of the connection of the side arm, one central external stent 14 which also encompasses the side arm and three external stents 16 and one internal stent 15 distal of the connection with the side arm 5. The internal and external stent are fastened to the tubular body by known methods including by stitching, adhesive or the like.

The stent graft depicted in FIG. 1 would normally have a diameter of the main tubular body of 12 mm and a diameter of the side arm of 8 mm. The stent graft shown in FIG. 1 is the longest that would normally be used in deployment into the iliac artery of a patient as will be discussed below.

Figure 2:
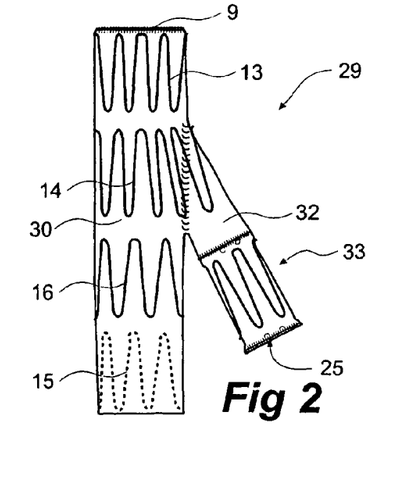
FIG. 2 shows a second embodiment of a stent graft of the present invention intended for use in the iliac artery.

FIG. 2 shows the shortest practical stent graft which can be deployed into a common iliac artery. The stent graft 29 depicted in FIG. 2 has a tubular body 30 and a side arm 32. In this embodiment there is one external stent 13 proximal of the junction with the side arm, one central external stent 14 which also encompasses the side arm and one external stent 16 and one internal stent 15 distal of the junction with the side arm. The stent graft depicted in FIG. 2 has a diameter of the main tubular body 30 of 12 mm and a diameter of the side arm 32 of 8 mm. The construction of the connection socket 33 on the stent graft shown in FIG. 2 is similar to that shown in FIG. 1.

For placement of a side branch stent graft into the internal iliac artery, the critical dimension is the distance from the proximal end 11 of the stent graft to the end 25 of the side arm 5 as this is the distance which must fit between the aortic bifurcation and the entrance to the internal iliac artery as will be discussed below.

Figure 3:
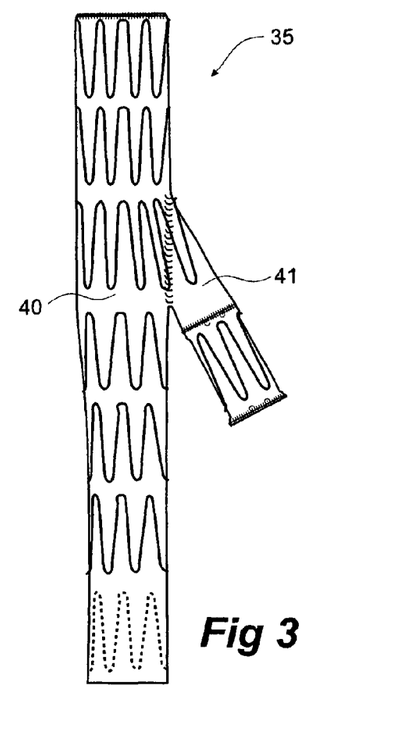
FIG. 3 shows a third embodiment of a stent graft of the present invention intended for use in the iliac artery.

FIG. 3 shows an alternative embodiment of stent graft 35 substantially similar to that shown in FIG. 1 except that the tubular body 40 is tapered to a diameter of 10 mm distal of the connection with the side arm 41 whereas the diameter of the tubular body 40 proximal of the connection is 12 mm.

Figure 4:
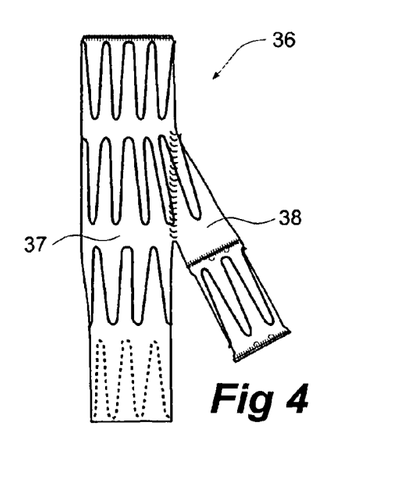
FIG. 4 shows a fourth embodiment of a stent graft of the present invention intended for use in the iliac artery.

Similarly in FIG. 4 the stent graft 36 has a tubular body 37 which is tapered distal of the side arm connection 38 to give a diameter of 10 mm whereas the diameter of the tubular body 37 proximal of the connection is 12 mm.

Figure 5:
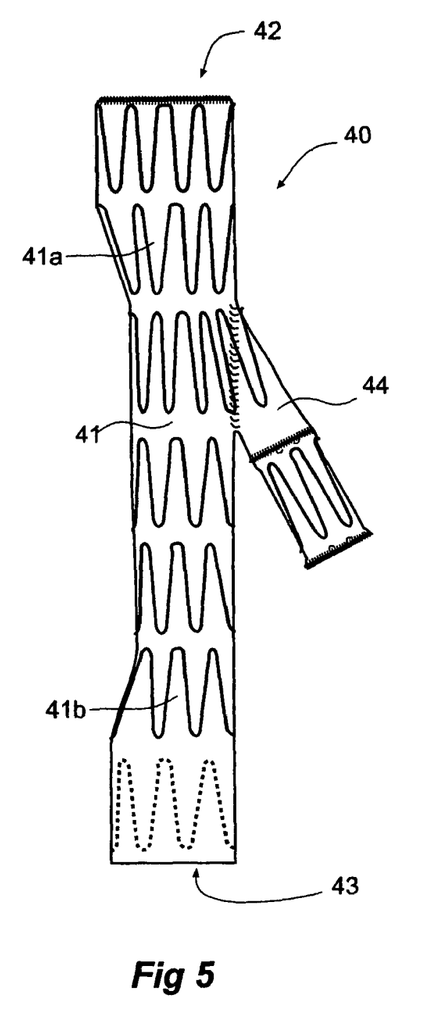
FIG. 5 shows a fifth embodiment of a stent graft of the present invention intended for use in the iliac artery.

FIG. 5 shows an alternative embodiment of stent graft 40 substantially similar to that shown in FIG. 1 except that the tubular body 41 is expanded to a diameter of 20 mm at its proximal end 42 proximal of the connection with the side arm 44 with a frusto-conical portion 41a joining the central portion to the proximal portion and also expanded to a diameter of 16 mm at its distal end 43 with a frusto-conical portion 41b joining the central portion to the distal portion.

Figure 6:
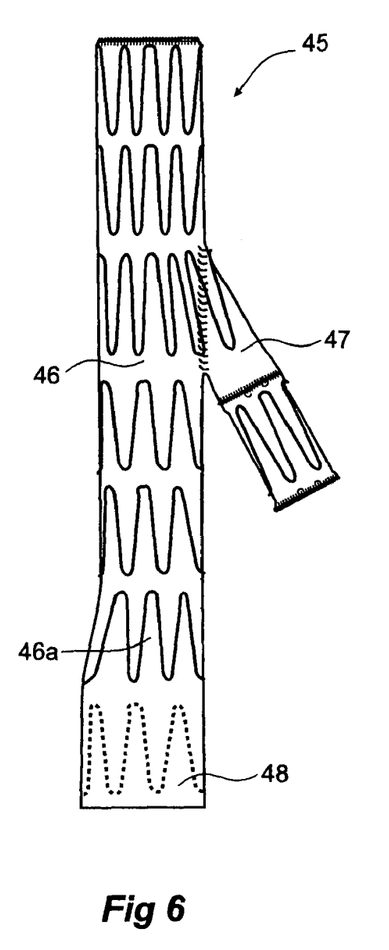
FIG. 6 shows a sixth embodiment of a stent graft of the present invention intended for use in the iliac artery.

Similarly in FIG. 6 the stent graft 45 has a tubular body 46 which is expanded distal of the side arm 47 connection to give a diameter of 16 mm at its distal end 48 with a frusto-conical portion 46a joining the central portion to the distal portion whereas the diameter of the tubular body proximal of the connection is 12 mm.

FIG. 7A to 7F shows schematically a range of sizes of stent grafts for the common iliac artery in stylised form. The position of stents is represented by a box on the stylised form.

FIG. 7A shows a schematic stent graft 50 with a proximal reinforcing ring 51, two external stents 52 proximal of the side arm 53, and central external stent 54, three external stents 55 distal of the side arm 53 and one internal distal-most stent 56. The stents 52 and 54 each have a length of 14 mm and are separated by a gap 57 of 2 mm. The stents 55 each have a length of 12 mm and are separated by a gap 58 of 5 mm. The stent 56 has a length of 17 mm and is separated from the stent 55 by a gap of 5 mm.

FIGS. 7B, 7C, 7D, 7E and 7F all show the various configurations of stent graft with varying numbers of stents proximal and distal of the side branch.

Table 1 shows a range of sizes of stent grafts and numbers and sizes of stents as depicted in FIGS. 7A to 7F. The overall length is the dimension 60 shown in FIG. 7A, the proximal length is the length 61 shown in FIG. 7A and the distal length is the length 62 shown in FIG. 7A.

TABLE 1

|  | FIG. 7A | FIG. 7B | FIG. 7C | FIG. 7D | FIG. 7E | FIG. 7F |
| --- | --- | --- | --- | --- | --- | --- |
| Overall Length (mm) | 119 | 102 | 85 | 103 | 86 | 69 |
| Proximal length (mm) | 61 | 61 | 61 | 45 | 45 | 45 |
| Distal length (mm) | 58 | 41 | 24 | 58 | 41 | 24 |
| Proximal Diameter (mm) | 12 | 12 | 12 | 12 | 12 | 12 |
| Central Diameter (mm) | 12 | 12 | 12 | 12 | 12 | 12 |
| Distal Diameter (mm) | 12 | 12 | 12 | 12 | 12 | 12 |
| Number of Stents on main body | 7 | 6 | 5 | 6 | 5 | 4 |
| Number of stents on main body proximal of side arm | 2 | 2 | 2 | 1 | 1 | 1 |
| Length of stents on main body proximal of side arm (mm) | 14 | 14 | 14 | 14 | 14 | 14 |
| Spacing of stents on main body proximal of side arm (mm) | 2 | 2 | 2 | 2 | 2 | 2 |
| Number of central external stents | 1 | 1 | 1 | 1 | 1 | 1 |
| Length of central external stents (mm) | 14 | 14 | 14 | 14 | 14 | 14 |
| Number of stents on main body distal of side arm | 4 | 3 | 2 | 4 | 3 | 2 |
| Length of external stents on main body distal of side arm (mm) | 12 | 12 | 12 | 12 | 12 | 12 |
| Length of distal most internal stent on main body (mm) | 17 | 17 | 17 | 17 | 17 | 17 |
| Spacing of stents on main body distal of side arm (mm) | 5 | 5 | 5 | 5 | 5 | 5 |
| Number of Stents on side arm | 1 | 1 | 1 | 1 | 1 | 1 |
| 12 mm Ring at proximal end | Yes | Yes | Yes | Yes | Yes | Yes |
| 7 mm Rings on side arm | Yes | Yes | Yes | Yes | Yes | Yes |

As discussed above, the proximal length is important as a stent graft must be able to be deployed with its distal end below the aortic bifurcation and the distal end of its side arm proximal of the iliac bifurcation between the internal and external iliac arteries.

Similarly FIGS. 8A to 8F show schematic configurations of stent grafts similar to that of the corresponding drawings in FIGS. 7A to 7F except that in FIGS. 8A to 8F the proximal end 70 of the stylised stent graft has a diameter of 12 mm and the distal end 71 is tapered to a diameter of 10 mm. The lesser diameter of the distal end of the stent graft in the embodiments of stent graft shown in FIGS. 8A to 8F allow for sealing into a smaller non-aneurysed region of the external iliac artery without exerting excessive pressure onto the walls of the vasculature.

Table 2 shows a range of sizes of stent grafts as depicted in FIGS. 8A to 8F. The overall length is the dimension 60 shown in FIG. 7A, the proximal length is the length 61 shown in FIG. 7A and the distal length is the length 62 shown in FIG. 7A.

TABLE 2

|  | FIG. 8A | FIG. 8B | FIG. 8C | FIG. 8D | FIG. 8E | FIG. 8F |
| --- | --- | --- | --- | --- | --- | --- |
| Overall Length (mm) | 119 | 102 | 85 | 103 | 86 | 69 |
| Proximal length (mm) | 61 | 61 | 61 | 45 | 45 | 45 |
| Distal length (mm) | 58 | 41 | 24 | 58 | 41 | 24 |
| Proximal Diameter (mm) | 12 | 12 | 12 | 12 | 12 | 12 |
| Central Diameter (mm) | 12 | 12 | 12 | 12 | 12 | 12 |
| Distal Diameter (mm) | 10 | 10 | 10 | 10 | 10 | 10 |
| Number of Stents on main body | 7 | 6 | 5 | 6 | 5 | 4 |
| Number of stents on main body proximal of side arm | 2 | 2 | 2 | 1 | 1 | 1 |
| Length of stents on main body proximal of side arm (mm) | 14 | 14 | 14 | 14 | 14 | 14 |
| Spacing of stents on main body proximal of side arm (mm) | 2 | 2 | 2 | 2 | 2 | 2 |
| Number of central external stents | 1 | 1 | 1 | 1 | 1 | 1 |
| Number of stents on main body distal of side arm | 4 | 3 | 2 | 4 | 3 | 2 |
| Length of central external stents (mm) | 14 | 14 | 14 | 14 | 14 | 14 |
| Length of external stents on main body distal of side arm (mm) | 12 | 12 | 12 | 12 | 12 | 12 |
| Length of distal most internal stent on main body (mm) | 17 | 17 | 17 | 17 | 17 | 17 |
| Spacing of stents on main body distal of side arm (mm) | 5 | 5 | 5 | 5 | 5 | 5 |
| Number of Stents on side arm | 1 | 1 | 1 | 1 | 1 | 1 |
| 12 mm Ring at proximal end | Yes | Yes | Yes | Yes | Yes | Yes |
| 7 mm Rings on side arm | Yes | Yes | Yes | Yes | Yes | Yes |

FIGS. 9A to 9D show schematic configurations of stent grafts similar to that of the corresponding drawings in FIGS. 7A to 7F except that in FIGS. 9A to 9D the proximal end 70 of the stylised stent graft has a diameter of 20 mm and the distal ends 71 have diameters of 12 mm and 16 mm.

Table 3 shows a range of sizes of stent grafts as depicted in FIGS. 9A to 9D. The overall length is the dimension 60 shown in FIG. 7A, the proximal length is the length 61 shown in FIG. 7A and the distal length is the length 62 shown in FIG. 7A.

TABLE 3

|  | FIG. 9A | FIG. 9B | FIG. 9C | FIG. 9D |
| --- | --- | --- | --- | --- |
| Overall Length (mm) | 119 | 119 | 102 | 102 |
| Proximal length (mm) | 61 | 61 | 61 | 61 |
| Distal length (mm) | 58 | 58 | 41 | 41 |
| Proximal Diameter (mm) | 20 | 20 | 20 | 20 |
| Central Diameter (mm) | 12 | 12 | 12 | 12 |
| Distal Diameter (mm) | 12 | 16 | 12 | 16 |
| Number of Stents on main body | 7 | 7 | 6 | 6 |
| Number of stents on main body proximal of side arm | 2 | 2 | 2 | 2 |
| Length of stents on main body proximal of side arm (mm) | 14 | 14 | 14 | 14 |
| Spacing of stents on main body proximal of side arm (mm) | 2 | 2 | 2 | 2 |
| Number of central external stents | 1 | 1 | 1 | 1 |
| Length of central external stents (mm) | 14 | 14 | 14 | 14 |
| Number of stents on main body distal of side arm | 4 | 4 | 3 | 3 |
| Length of external stents on main body distal of side arm (mm) | 12 | 12 | 12 | 12 |
| Length of distal most internal | 17 | 17 | 17 | 17 |

TABLE 3-continued

| | FIG. 9A | FIG. 9B | FIG. 9C | FIG. 9D |
|---|---|---|---|---|
| stent on main body (mm) | | | | |
| Spacing of stents on main body distal of side arm (mm) | 5 | 5 | 5 | 5 |
| Number of Stents on side arm | 1 | 1 | 1 | 1 |
| 20 mm Ring at proximal end | Yes | Yes | Yes | Yes |
| 7 mm Rings on side arm | Yes | Yes | Yes | Yes |

Figure 10:
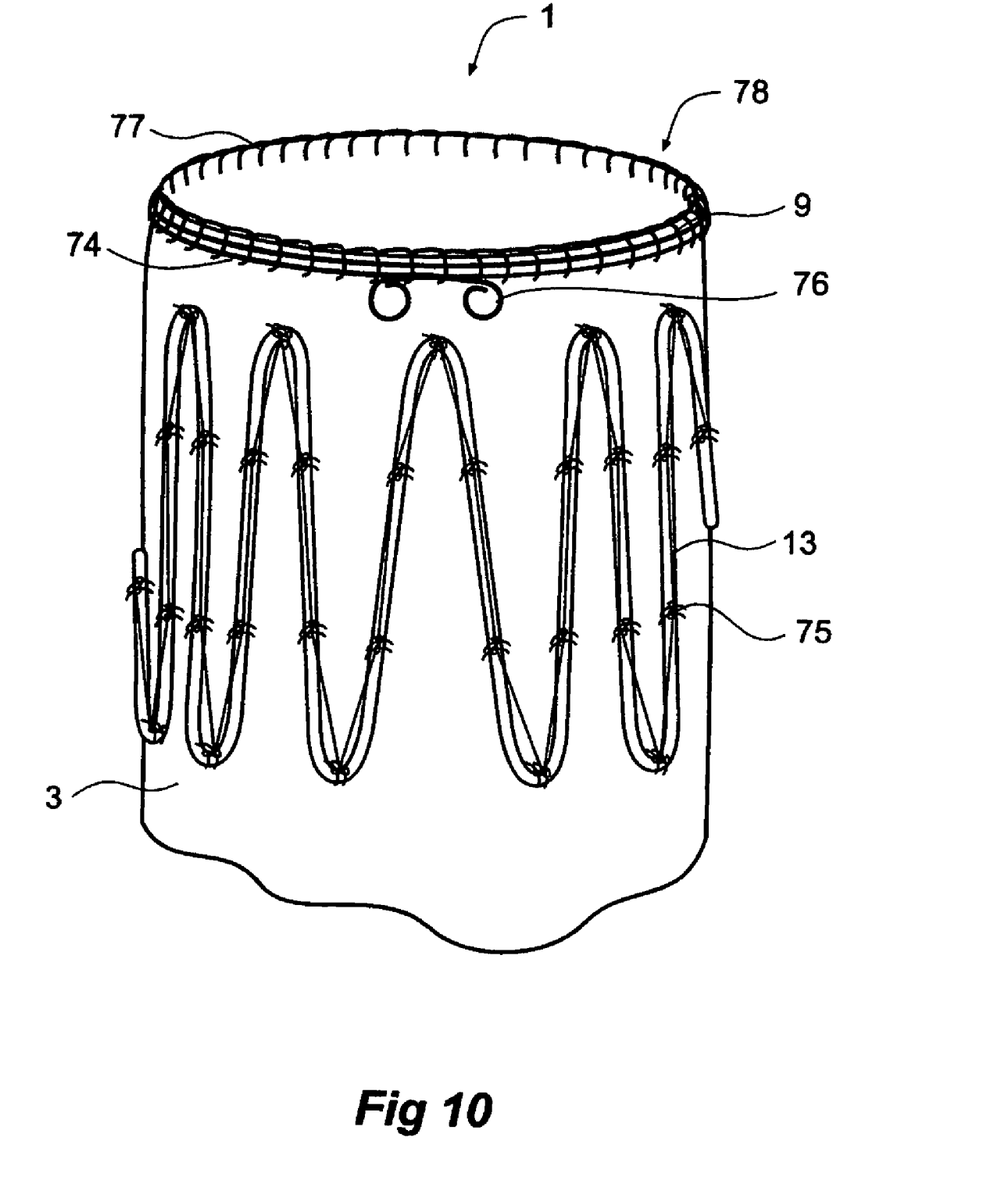
FIG. 10 shows a detail of the proximal end of stent graft of the present invention.

FIG. 10 shows the construction of a stent graft according to the present invention with a proximal reinforcing ring. The same reference numerals as used in FIG. 1 are used for FIG. 10 for the corresponding components. The tubular body 3 of the stent graft 1 has a proximal-most external stent 13 stitched onto the tubular body by means of stitches 75. At the proximal end 78 of the stent graft 1 a reinforcing ring 9 is provided. The reinforcing ring 9 comprises two turns of a shape memory wire 74, such as Nitinol™ wire, around the proximal end 78 and loops 76 at each terminal end of the Nitinol™ wire 74. The loops 76 are provided to prevent the ends of the Nitinol™ wire causing damage to the vasculature in which they are deployed. The two turns of Nitinol™ wire 74 are stitched by means of stitching 77 to proximal end the tubular body 3.

The Nitinol™ reinforcing ring 9 provides reinforcement for the proximal end of the stent graft so that when a catheter or other device is being deployed into the proximal end of the stent graft the end of the stent graft cannot be damaged. The Nitinol™ reinforcing ring 9 provides a fixed diameter into which another self expanding or balloon expandable stent graft can expand or be expanded within the proximal end of the stent graft 1.

Figure 11:
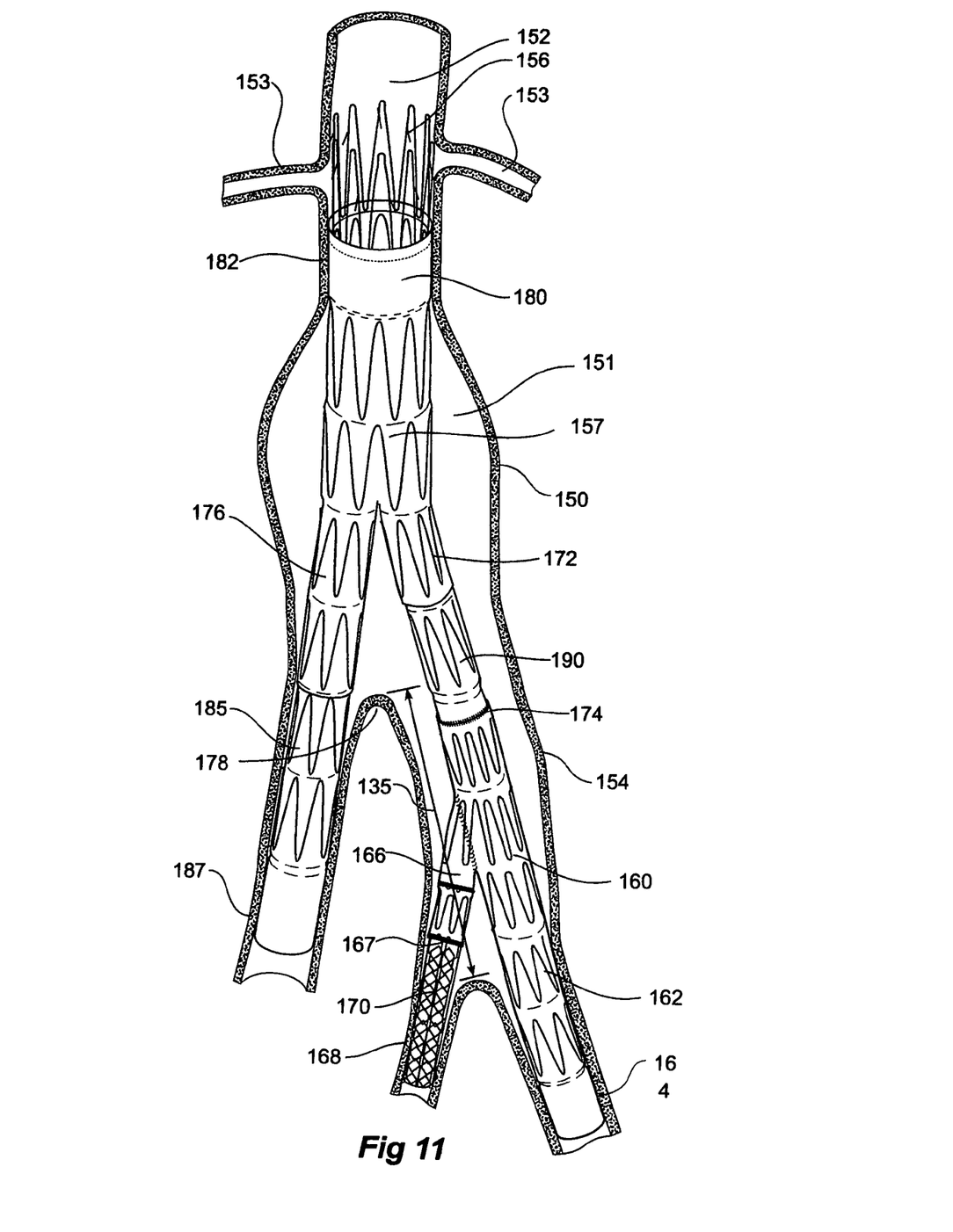
FIG. 11 shows schematically a cross section of an aneurysed aorta and common iliac artery with a composite stent graft system deployed into it including the iliac stent graft of the present invention.

FIG. 11 shows a full assembly of a composite stent graft system into an aneurised aortic and common iliac artery using the stent graft of the present invention for the common iliac artery.

The vasculature illustrated generally consists of a descending aorta 152 extending down to renal arteries 153 and further extending as the infra-renal aorta 150 down to an aortic bifurcation 178 and into the iliac and contra-iliac arteries 154 and 187. The common iliac artery 154 further bifurcates into an external iliac artery 164 and an internal iliac artery 168. It is this internal iliac artery 168 which is described above as a blind artery as endovascular access is only available via the common iliac artery. An aneurysed region 151 of the aorta 150 extends down into the common iliac artery 154.

In FIG. 11 the aorta 150 has an aneurism 151 which extends from below the renal arteries 153 into the common iliac artery 154. The aorta 152 proximal of the renal arteries 153 is not aneurised and provides a suitable landing zone for a proximally extending external stent 156 of a bifurcated stent graft 157.

The general order of placement of such a stent graft assembly for an aneurised aorta is first that the iliac branch stent graft 160 is placed first with its distal end 162 placed into a non-aneurised region of the external iliac artery 164. The side arm 166 extends towards the internal iliac artery 168. Subsequent to placement of the iliac branched stent graft 160 a covered leg extension 170 is placed extending from the side branch 166 so that it extends into and seals in the internal iliac artery 168. The covered leg extension 170 can be a covered balloon expandable stent or a covered self expanding stent.

The main bifurcated stent graft 157 is then deployed through the contra-lateral iliac artery 187 so that its longer leg 176 extends down the contra-lateral iliac artery 187 and its shorter leg 172 terminates proximal of the reinforcing ring 174 on the iliac stent graft 160 and proximal of the aortic bifurcation 178. The proximal end of the bifurcated stent graft 157 seals into a landing zone in the region of aorta 182 just distal of the renal arteries 153 and the proximally extending supra-renal external stent 156 extends over the renal arteries to the aorta region 152 to provide good support for the bifurcated stent graft. A leg extension 190 can then be deployed to connect the shorter leg 172 of the main bifurcated stent graft 157 to the reinforcing ring 174 on the iliac stent graft 160. In a final deployment stage a leg extension 185 can deployed into the longer leg 176 to seal into a non-aneurised portion of the contra-lateral common iliac artery 187 if the longer leg does not already seal onto such a zone.

By this arrangement a stent graft is effectively bridging the aneurised region by sealing in the non-aneurised portion of the aorta as well as in the non-aneurised portions of the iliac arteries.

Figure 7:
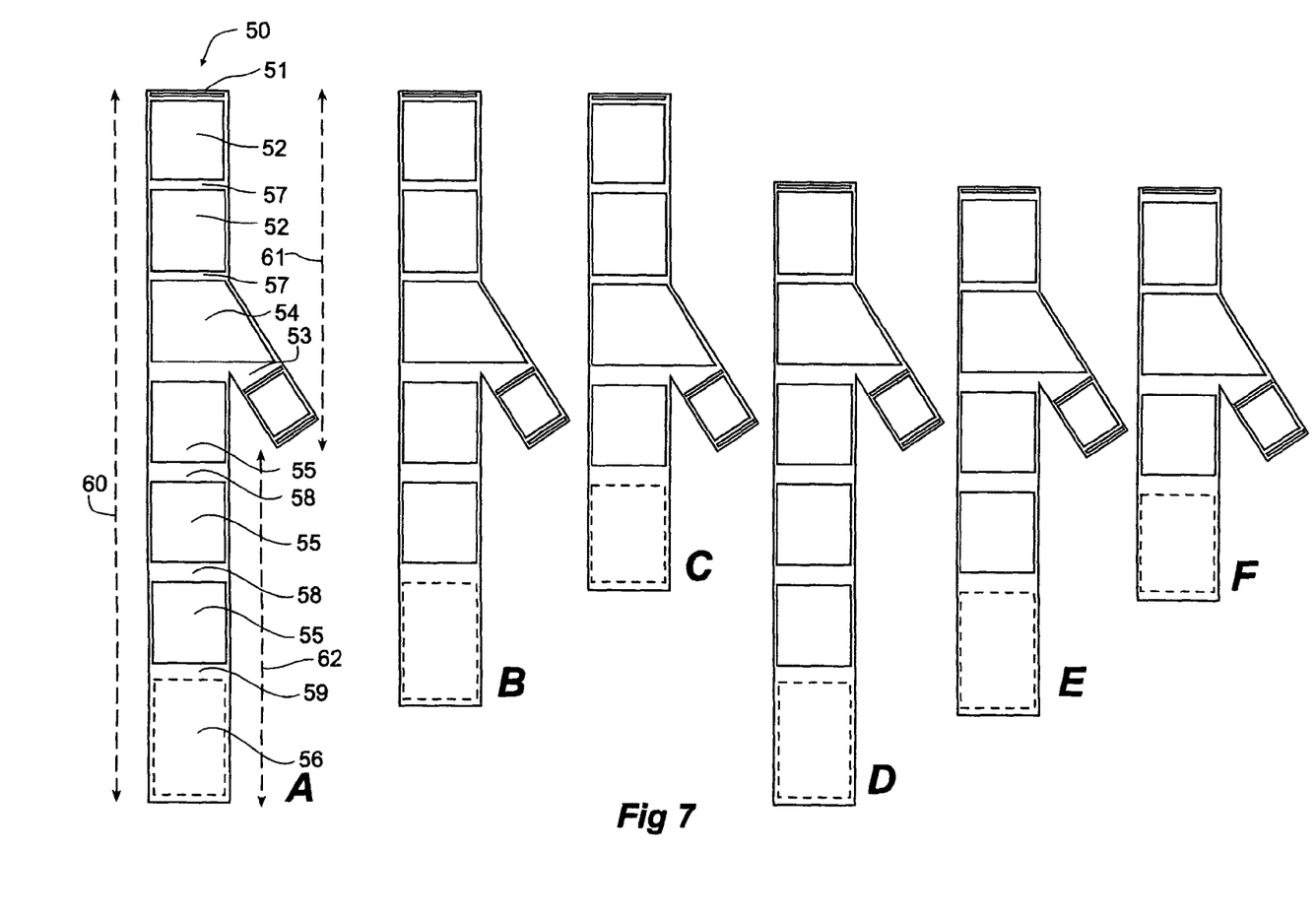
FIGS. 7A to 7F show schematically a first range of configurations of stent grafts of the present invention intended for use in the iliac artery.
Figure 8:
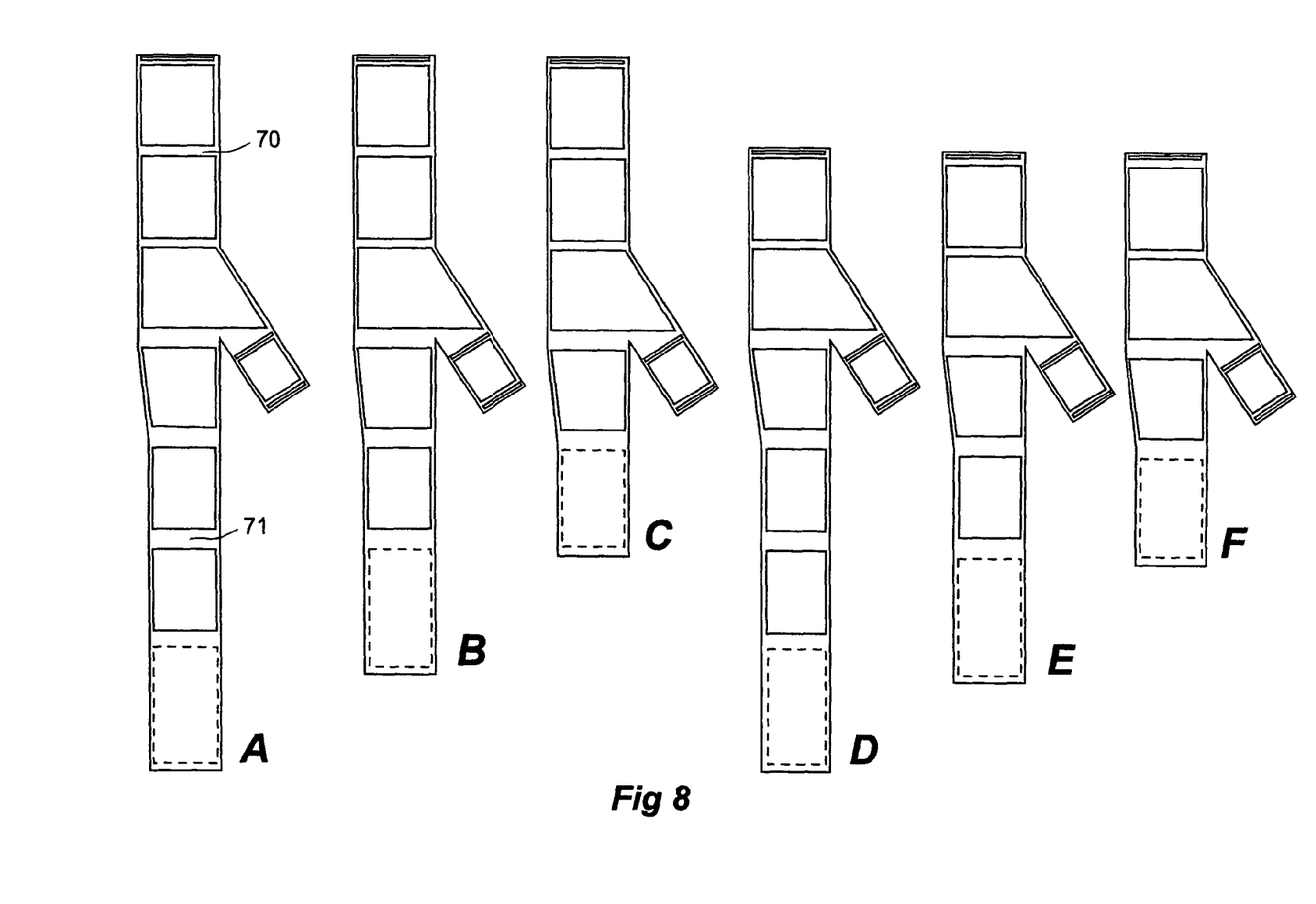
FIGS. 8A to 8F show schematically an alternative range of configurations of stent grafts of the present invention intended for use in the iliac artery.
Figure 9:
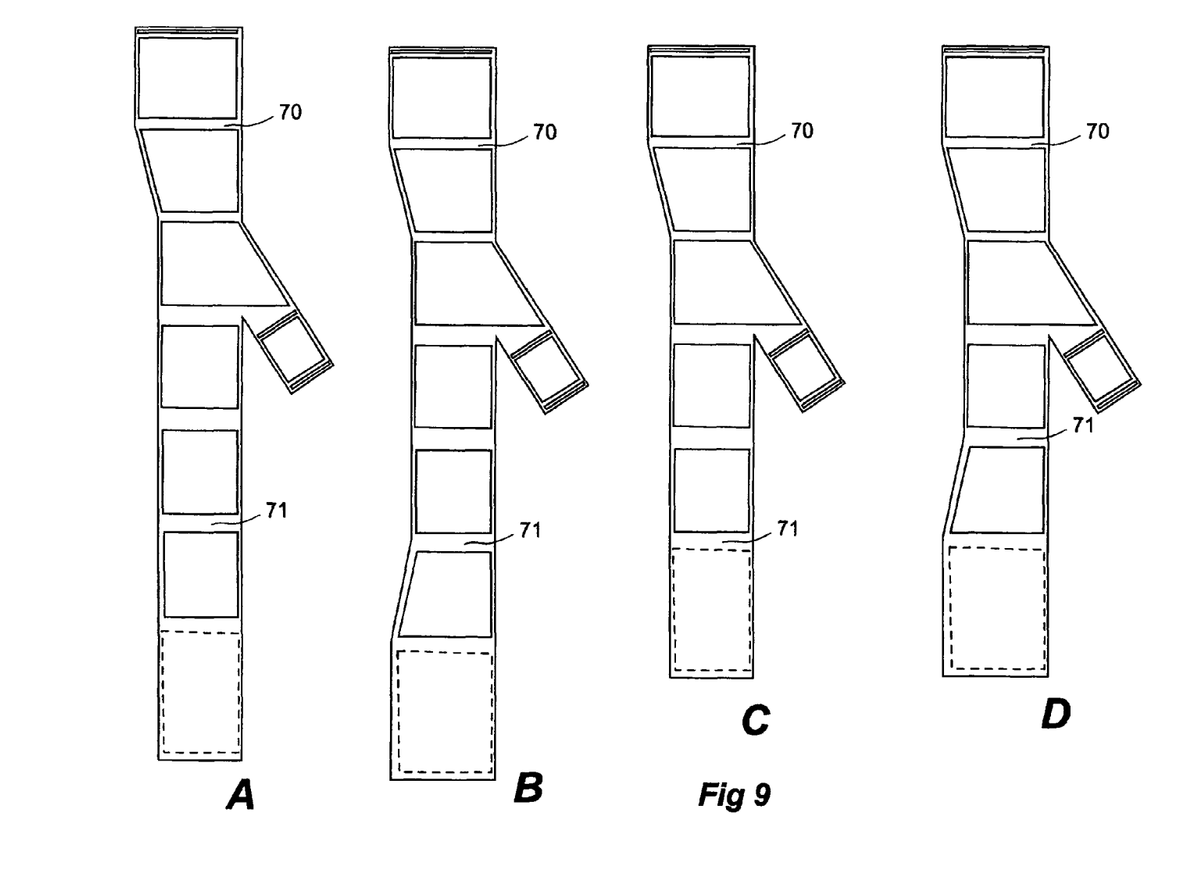
FIGS. 9A to 9D show schematically an alternative range of configurations of stent grafts of the present invention intended for use in the iliac artery.

The critical dimension in relation to deployment of a stent graft into an aneurised iliac artery 154 is the distance shown as 135 in FIG. 11. This is the distance from the iliac bifurcation 178 down to the bifurcation of the external iliac artery 164 and the internal iliac artery 168. The proximal length of a stent graft of the type discussed in relation to FIGS. 1 to 6 and as shown in FIGS. 7 to 9 must be less than the distance 135 so that access over the aortic bifurcation is possible to endovascularly enter the proximal end 174 of the stent graft 160 and the end 167 of the side branch 166 of the stent graft 160 must be placed so that a guide wire (not shown) can extend out of the side branch 166 and be manipulated into the internal iliac artery 168.

The length of the distal portion 162 of the stent graft 160 must be such that it can extend to non-aneurised region of the external iliac artery 164 so that a seal may be obtained with the distal end of the stent graft 160. Where the aneurism extends some distance down the external iliac artery a further leg extension may be placed so that the stent graft assembly extends through non-aneurised region of the external iliac artery.

Throughout this specification various indications have been given as to the scope of this invention but the invention is not limited to any one of these but may reside in two or more of these combined together. The examples are given for illustration only and not for limitation.

Throughout this specification and the claims that follow, unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A side branch stent graft comprising a main tubular body of a biocompatible graft material and having a main lumen therethrough, a tubular side branch having a side branch lumen therethrough, the tubular side branch being stitched to the main tubular body so that the side branch lumen is in fluid communication with the main lumen, the tubular side branch extending from the main tubular body at an acute angle thereto, the tubular side branch comprising a proximal end where it is stitched to the main tubular body and a distal end, at least one external proximal zig-zag self expanding stent on the main tubular body proximal of the tubular side branch, at least one distal external zig-zag self expanding stent on the main tubular body distal of the tubular side branch, one internal zig-zag self expanding stent at the distal end of the main tubular body, a central external zig-zag self expanding stent which extends around both the main tubular body and the proximal end of the tubular side branch, and a reinforcing ring around the proximal end of the main tubular body and stitched thereto, the reinforcing ring around the proximal end of the tubular body comprises at least two turns of shape memory wire, each end of the shape memory wire terminating in a loop, the tubular side branch comprising a connection socket for an extension stent graft at the distal end of the tubular side branch, the connection socket comprising a first reinforcing ring around the tubular side branch at the distal end thereof, a second reinforcing ring spaced apart along the tubular side branch from the first ring and a connection socket zig zag resilient stent between the first and second reinforcing rings.

2. A side branch stent graft as in claim 1 comprising either one or two of the proximal external zig-zag stents on the main tubular body.

3. A side branch stent graft as in claim 1 comprising from one to three of the distal external zig-zag stents on the main tubular body.

4. A side branch stent graft as in claim 1 wherein the connection socket zig zag resilient stent and the first and second rings are on the outside of the tubular body.

5. A side branch stent graft as in claim 1 wherein the first and second rings comprise shape memory wire.

6. A side branch stent graft as in claim 1 wherein the first and second rings comprise at least two turns of wire with each end terminating in a loop.

7. A side branch stent graft as in claim 1 wherein the zig zag resilient stent comprises a shape memory wire and the zig zag resilient stent defines a cylindrical form having a diameter less than that of the tubular side branch whereby to define a self contracting stent.

8. A side branch stent graft as in claim 1 wherein the acute angle is in the range of from 15 to 45 degrees.

9. A side branch stent graft as in claim 1 wherein the or each external zig-zag stents proximal of the tubular side branch has a length of 14 mm and are spaced apart by about 2 mm.

10. A side branch stent graft as in claim 1 wherein the or each external zig-zag stents distal of the tubular side branch has a length of 12 mm and are spaced apart by about 5 mm.

11. A side branch stent graft as in claim 1 wherein the central external zig-zag stent has a length of 14 mm and is spaced apart from the nearest stent proximal to it by about 2 mm and from the nearest stent distal of it by about 5 mm.

12. A side branch stent graft as in claim 1 wherein the main tubular body has a diameter of about 12 mm and the tubular side branch has a diameter of about 8 mm.

13. A side branch stent graft as in claim 1 wherein the main tubular body has a diameter of about 12 mm proximal of the tubular side branch and a diameter distal of the tubular side branch of about 10 mm.

14. A side branch stent graft as in claim 1 wherein the main tubular body has a diameter of about 20 mm proximal of the tubular side branch and a diameter distal of the tubular side branch of about 16 mm.

15. A side branch stent graft as in claim 1 wherein the main tubular body has a length of about 69 mm to 119 mm and the tubular side branch has a length of about 25 mm.

16. A side branch stent graft as in claim 1 wherein the stent graft has a length from its proximal end to the distal end of the tubular side branch of about 45 mm to 61 mm.

17. A side branch stent graft as in claim 1 wherein the stent graft has a length from its distal end to the distal end of the tubular side branch of about 24 mm to 58 mm.

* * * * *